(12) United States Patent
Lapinlampi et al.

(10) Patent No.: US 7,630,758 B2
(45) Date of Patent: Dec. 8, 2009

(54) SEPARATION OF NATURAL AND DRUG-INDUCED SLEEP OF A SUBJECT

(75) Inventors: Petteri Lapinlampi, Espoo (FI); Mika Sarkela, Helsinki (FI)

(73) Assignee: General Electric Company, Schenectady, NY (US)

( * ) Notice: Subject to any disclaimer, the term of this patent is extended or adjusted under 35 U.S.C. 154(b) by 505 days.

(21) Appl. No.: 11/473,223

(22) Filed: Jun. 22, 2006

(65) Prior Publication Data

US 2008/0009753 A1   Jan. 10, 2008

(51) Int. Cl.
*A61B 5/00* (2006.01)

(52) U.S. Cl. ................................. 600/544; 600/300

(58) Field of Classification Search .................. None
See application file for complete search history.

(56) References Cited

U.S. PATENT DOCUMENTS

| | | | |
|---|---|---|---|
| 5,280,791 | A | 1/1994 | Lavie |
| 6,319,205 | B1 | 11/2001 | Goor et al. |
| 2002/0173729 | A1 | 11/2002 | Viertio-Oja et al. |
| 2003/0004423 | A1 | 1/2003 | Lavie et al. |
| 2006/0058700 | A1* | 3/2006 | Marro et al. ............... 600/554 |
| 2006/0217628 | A1* | 9/2006 | Huiku ....................... 600/544 |

FOREIGN PATENT DOCUMENTS

| | | |
|---|---|---|
| WO | WO 2004 034897 A1 | 4/2004 |
| WO | WO 2006 026528 A2 | 3/2006 |

OTHER PUBLICATIONS

*Sympathetic-Nerve Activity during Sleep in Normal Subjects*, Virend K. Somers, et al., The New England Journal of Medicine, vol. 328:303-307, Feb. 7, 1993.

E.R.J. Seitsonen et al, EEG Spectral Entropy, Heart Rate, Photoplethysmography and Motor Responses to Skin Incision During Sevoflurane Anaesthesia, ACTA Anaesthesiologica Scandinavica vol. 49, No. 3, Mar. 2005, pp. 284-292, Denmark.

Willie Bosseau Murray et al, The Peripheral Pulse Wave: Information Overlooked, Journal of Clinical Monitoring, Sep. 1996, 365-377, vol. 12, No. 5, Kluwer Academic Publishers, Netherlands.

* cited by examiner

*Primary Examiner*—Robert L Nasser
(74) *Attorney, Agent, or Firm*—Andrus, Sceales, Starke & Sawall, LLP (57) ABSTRACT

The invention relates to a mechanism for detecting whether a sleep state of a subject is due to natural sleep or induced by drugs. An indicator indicative of the activation of the autonomic nervous system of the subject is derived based on cardiovascular signal data measured from the subject and the indicator is employed to identify whether the sleep of the subject is drug-induced sleep or natural sleep. The identification is performed upon detection of a sleep state.

25 Claims, 5 Drawing Sheets

SEPARATION OF NATURAL AND DRUG-INDUCED SLEEP OF A SUBJECT

FIELD OF THE INVENTION

The present invention relates generally to the monitoring of a subject that appears to be in sleep. More particularly, the present invention relates to a mechanism for separating natural sleep from drug-induced unconsciousness.

BACKGROUND OF THE INVENTION

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity by recording and analyzing the weak biopotential signals generated in the cortex of the brain with electrodes attached on the skin of the skull surface. The EEG has been in wide use for decades in basic research of the neural systems of the brain, as well as in clinical diagnosis of various neurophysiological diseases and disorders.

One field of application for EEG measurement is sleep analysis. Various EEG-based methods have been designed for automated sleep classification, for example, which allow sleep to be divided into different stages according to its depth.

The autonomic nervous system (ANS) is the 'unconscious' nervous system, which controls and regulates virtually all of our basic body functions, such as cardiac function, blood circulation and glandural secretion. The main parts of the ANS are the parasympathetical and sympathetical nervous branches. The sympathetic nervous system (SNS) usually prepares us for high stress situations by speeding up the body functions. Under conditions of normal ANS regulation, the parasympathetic system restores the normal conditions in blood circulation by slowing down the heart rate. Pain and discomfort, for example, may activate the SNS and cause an increase in blood pressure, heart rate, and adrenal secretions.

Heart rate variability (HRV) has traditionally been used as a surrogate measure of autonomic activation. Low frequency (LF) components of an HRV signal correspond to both sympathetic and parasympathetic activity, while higher frequency (HF) components correspond to parasympathetic activity only. Thus, the ratio of the LF components to the HF components (LF/HF), so-called sympatho-vagal ratio, can be used to quantify the level of sympathetic activation.

Various parameters indicative of the activity of the ANS or SNS have also been utilized in sleep analysis. U.S. Pat. No. 5,280,791, for example, discloses a method for separating REM sleep and non-REM sleep based on HRV variables derived from an ECG signal. U.S. Pat. No. 6,319,205 in turn discloses a method for detecting REM sleep by measuring peripheral arterial tone. In this method, a static pressure field is applied around the distal part of a digit of a subject and changes in the peripheral arterial tone are monitored.

Generally, anesthetic agents affect the functioning of the autonomic nervous system. Anesthetics mainly depress autonomic activity, which can be seen, for example, as dropping of the blood pressure and depression of the total HRV power. Propofol, for example, which is a rather pure hypnotic drug, has been reported to reduce both sympathetic and parasympathetic tone. Midazolam in turn is associated with lowered LF and HF powers as compared to baseline levels, while dexmedetomidine decreases sympathetic tone with attenuation of hemodynamic responses to anesthesia and surgery. Similar effects are observed with the smaller doses associated with sedation.

Drug-induced unconsciousness and natural sleep produce EEG patterns that are quite similar to each other. The discrimination of these states based on the EEG signal is therefore impossible with current methods, at least in short time windows of a few minutes. Dexmedetomidine, for example, has attracted attention as a sedative agent due to its ability to induce a state which is quite similar to non-REM sleep. The EEG patterns measured under the influence of sedative/anesthetic drugs (e.g. dexmedetomidine, propofol and midazolam) and during natural sleep are very much alike.

Due to the EEG resemblances, the current sleep monitoring methods are incapable of separating drug-induced unconsciousness from natural sleep. However, such an ability would provide clinicians extra information in various situations in which a patient appears to be in sleep but it is not clear whether the state of unconsciousness is caused by drugs or natural sleep.

The present invention seeks to eliminate the above drawback and to accomplish a mechanism capable of separating drug-induced unconsciousness from natural sleep.

SUMMARY OF THE INVENTION

The present invention seeks to provide a novel mechanism for monitoring a subject whose consciousness of the surrounding world is suspended. More particularly, the present invention seeks to provide a mechanism that indicates whether the suspended consciousness of a patient is caused by natural sleep or induced by drugs, i.e. a mechanism that allows the separation of natural sleep from drug-induced unconsciousness. Drugs here refer mainly to drugs used in general anesthesia and sedation.

The present invention is based on the fact that a clear difference exists in the autonomic effects during natural and drug-induced sleep. In the present invention, at least cardiovascular signal data, and typically also brain wave signal data, is measured from a subject. Cardiovascular signal data here refers to a signal indicative of the function of the cardiovascular system of the subject. A measure derived from the cardiovascular signal data and indicative of the autonomic activation of the subject is employed to detect whether the unconscious state is due to natural sleep or induced by drugs. Simultaneous measurement of the brain wave signal data enables an automated monitoring system: when the brain wave measurement indicates that the subject is in sleep, the process examines whether the said measure indicates drug-induced sleep or natural sleep.

As discussed below, in a typical embodiment a plethysmographic (PG) signal, especially a photoplethysmographic (PPG) signal, serves as the cardiovascular signal and the said measure derived from the signal is the coefficient of variation of the plethysmographic pulse amplitude.

Thus one aspect of the invention is providing a method for separating natural sleep from drug-induced unconsciousness. The method includes the steps of obtaining cardiovascular signal data from a subject, the cardiovascular signal data being indicative of the function of the cardiovascular system of the subject, deriving, based on the cardiovascular signal data, an indicator indicative of the activation of the autonomic nervous system of the subject, and identifying, based on the indicator, whether the sleep is drug-induced sleep or natural sleep.

Another aspect of the invention is that of providing an arrangement for separating natural sleep from drug-induced unconsciousness. The arrangement includes first measurement means for obtaining cardiovascular signal data from a subject, the cardiovascular signal data being indicative of the function of the cardiovascular system of the subject, calculation means for deriving, based on the cardiovascular signal data, an indicator indicative of the activation of the autonomic nervous system of the subject, and identification means for identifying, based on the indicator, whether the sleep is drug-induced sleep or natural sleep.

The solution of the invention provides an uncomplicated method for ascertaining whether the unconsciousness of a subject is induced by drugs or due to natural sleep. In a post anesthetic care unit, for example, the system of the invention may therefore evaluate whether a patient is sleeping naturally or whether earlier administered anesthetics or sedatives still contribute to her or his unconsciousness. Furthermore, the nursing staff may continuously supervise the sleep state of the patient without a constant need to be at the bedside.

In a further embodiment of the invention, the specificity of the method may be improved by further detecting whether a subject whose unconsciousness is detected to be caused by natural sleep is in a REM or non-REM sleep.

A further aspect of the invention is that of providing a computer program product. The program product may be utilized to upgrade known monitoring devices in an environment where cardiovascular signal data is available. The computer program product includes a first program code portion configured to derive, based on cardiovascular signal data measured from a subject, an indicator indicative of the activation of the autonomic nervous system of the subject, and a second program code portion configured to identify, based on the indicator, whether the sleep is drug-induced sleep or natural sleep.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 6 in the appended drawings, wherein:

FIGS. 5b and 5c illustrate the entropy and the PPGA variability, respectively, measured during the sleep stages shown in FIG. 5a.

DETAILED DESCRIPTION OF THE INVENTION

Figure 1:
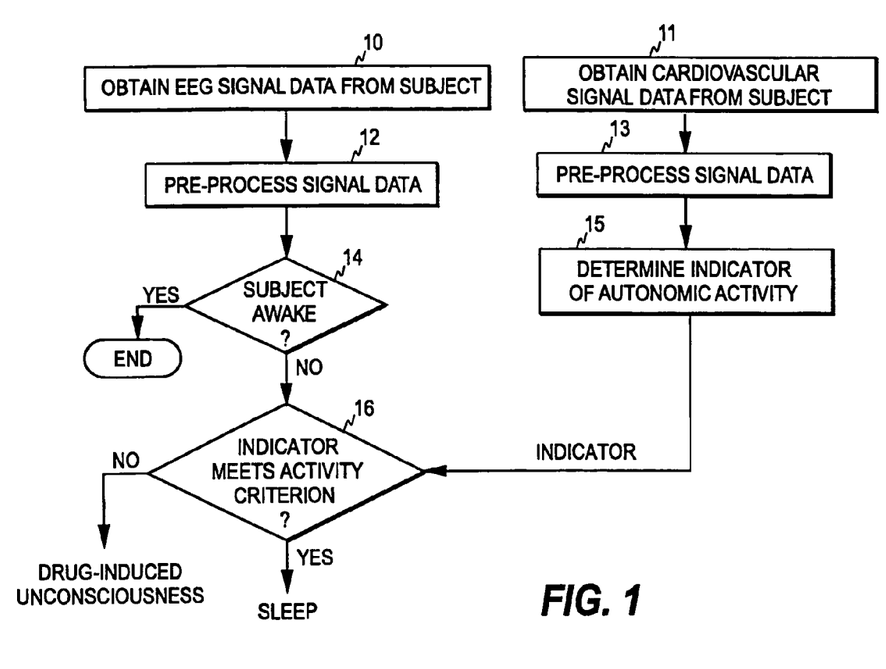
FIG. 1 is a flow diagram illustrating the outline of an automated monitoring method of the invention.

FIG. 1 illustrates the outline of an automated monitoring method of the invention. Two measurements are performed simultaneously on a subject: a brain wave measurement, typically an EEG measurement, and a cardiovascular measurement. Accordingly, separate EEG and cardiovascular signals are first acquired from the subject (steps 10 and 11, respectively).

As discussed below, the cardiovascular signal, which is indicative of the function of the cardiovascular system of the patient, is typically a photoplethysmographic (PPG) signal, but may also be an ECG signal or a blood pressure (BP) signal, for example.

The cardiovascular system here refers to the system including the heart, veins, arteries, and blood. The functions of the cardiovascular system induce a plurality of physiological signals that may be recorded to obtain information of the cardiovascular status of the subject. Such physiological signals include signals indicative of the peripheral blood circulation of the subject, such as a plethysmographic signal or a blood pressure signal. Blood pressure pulsation caused by the beating heart or air pressure variations in the lungs, for example, is mediated to the peripheries of the body through the vascular system. The tone of the vascular system regulates the conduction of the pulsation. Changes in the vascular tone form an independent source of pulsation detected in the peripheries of the body. Typical peripheral locations for the recording of the pulsation are finger tips and ear lobes. Therefore, most of the signals indicative of the function of the cardiovascular system, such as a PPG signal or a BP signal, are also indicative of the pulsative component of the peripheral blood circulation.

The measurement of the EEG and cardiosvascular signals may be implemented in a conventional manner, i.e. while the patient is connected to a patient monitoring system, the signal waveform data is recorded and stored in a memory of a monitoring device. As common in the art, the biosignals obtained from the electrodes are digitized and the digitized signal samples are processed as sets of sequential signal samples representing finite time blocks or time windows, commonly termed "epochs". Since the cardiovascular signal contains frequencies lower than the frequencies contained in the EEG signal, the time window used for the cardiovascular measurement is typically longer than the time window of the EEG measurement.

Prior to the actual processing, the recorded data may be pre-processed (steps 12 and 13, respectively) for filtering out some of the frequency components of the signal or for rejecting artifacts, for example. These steps are not necessary, but may be performed to improve the quality of the measured signal data.

Based on the cardiovascular signal, an indicator of autonomic activity is determined at step 15. The said indicator here refers to a variable that indicates, directly or indirectly, activation of the ANS. Although the indicator typically reflects changes in the sympathetic activation, generally speaking both the sympathetic and parasympathetic branches of the ANS may simultaneously have an effect on the indicator (sympathetic activation corresponds to parasympathetic inhibition, for example).

Based on the EEG measurement, a decision is made at step 14 whether the subject is awake or not. If the EEG measurement indicates that the subject is unconscious, i.e. not awake, the process employs the indicator of autonomic activity to determine whether the unconsciousness is caused by natural sleep or induced by drugs. This is implemented by examining whether the indicator of autonomic activity meets a predetermined activity criterion (step 16). If this is the case, the process decides that the unconsciousness is caused by natural sleep (step 16/yes). In the opposite case, the process concludes that the unconsciousness is induced by drugs (step 16/no).

If the EEG measurement indicates that the subject is awake, the process omits the examination of the indicator of the autonomic activity.

As discussed below, the decision at step 14 may be made based on various parameters derived from the EEG signal data.

Figure 2:
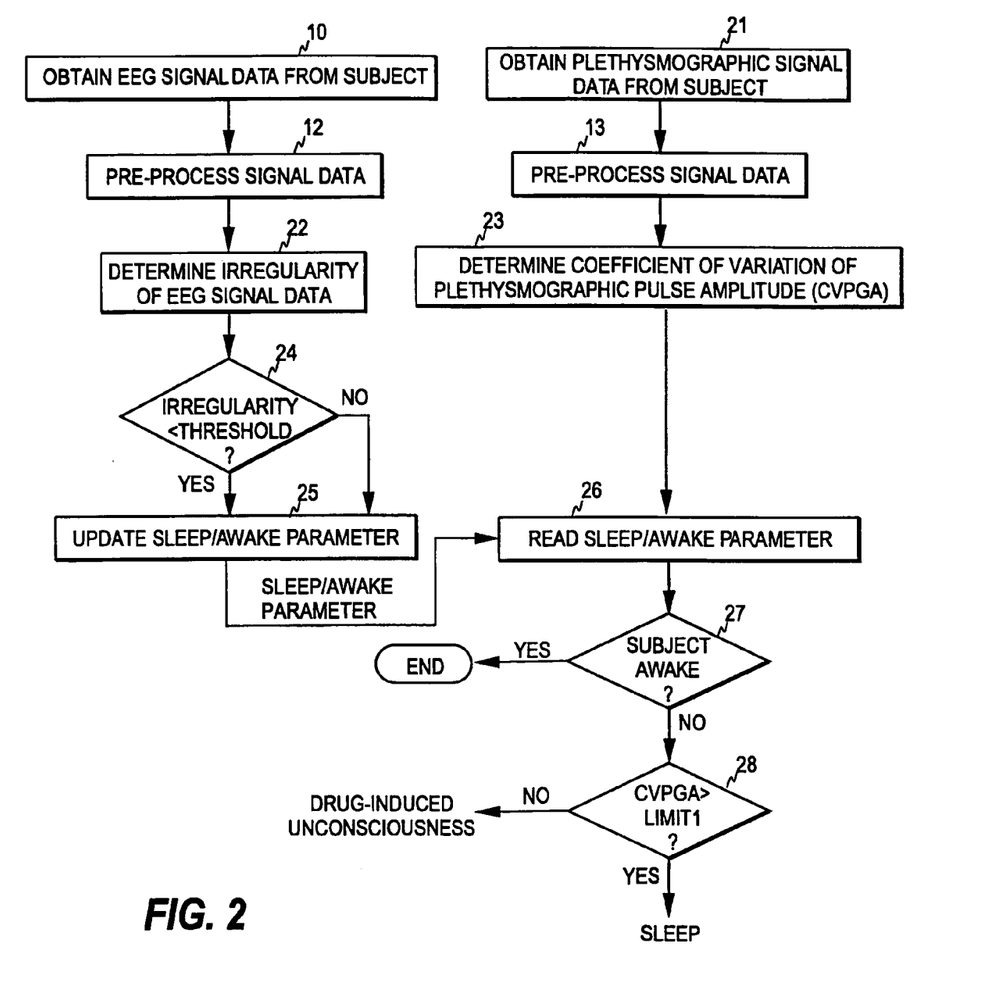
FIG. 2 is a flow diagram illustrating one embodiment of the method of the invention.

FIG. 2 illustrates an embodiment, in which the cardiovascular signal data acquired from the subject is plethysmographic signal data, cf. step 21, especially photoplethysmographic signal data which may be measured from finger, ear, or toe. Furthermore, in this embodiment the decision whether the subject is awake is based on the irregularity of the EEG signal data.

Based on the pre-processed EEG signal data obtained from step 12, entropy values of the EEG signal data are calculated in successive time windows (epochs) at step 22. In this example, entropy refers to spectral entropy, i.e. the pre-processed EEG signal data is subjected to a spectral decomposition, which may be carried out, for example, by a Fourier transform. However, several other types of entropies may also be utilized, such as Shannon entropy or approximate entropy. Furthermore, instead of different types of entropies step 22 may include the determination of a parameter related to the amount of irregularity in the EEG signal data. Other possible quantifications that may be used in this context include fractal spectrum analysis, Lempel-Ziv complexity, or spectral, bispectral, multispectral or stationarity analyses. Consequently, step 22 outputs a sequence of a parameter indicative of the irregularity of the EEG signal data and thus also of the hypnotic state of the subject. This parameter is compared with a predetermined threshold value at step 24 to examine whether the parameter value is below the said threshold. If this is the case, the process concludes that the subject is in sleep. In the opposite case, the subject is regarded as being awake. It is assumed here that for indicating the sleep/awake state of the subject a sleep/awake parameter is maintained and updated based on the EEG measurement (step 25).

Based on the pre-processed PG signal data obtained from step 13, a coefficient of variation of plethysmographic pulse amplitude (CVPGA) is calculated in successive time windows (epochs) at step 23. The CVPGA may be calculated from the time series of the measured plethysmographic pulse amplitude as follows:

$$CVPGA = \frac{SD}{Mean} * 100\%,$$

where SD is the standard deviation of the plethysmographic pulse amplitude values within a time window (epoch) and Mean is the corresponding mean value.

The value of the sleep/awake parameter is read at step 26. If the parameter indicates that the subject is in sleep (step 27/no), the process compares the CVPGA value with a first predetermined limit value at step 28. If the CVPGA value exceeds the limit value, the process concludes that the subject is sleeping naturally and if the CVPGA value is below the said limit value, the process concludes that drug-induced unconsciousness is in question.

Figure 3A:
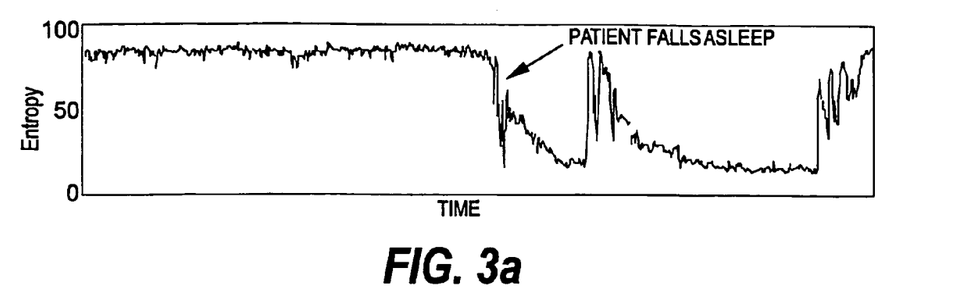
FIG. 3a to 3c illustrate the entropy, the PPG amplitude (PPGA), and the PPGA variability, respectively, measured according to the embodiment of FIG. 2 from a subject falling asleep under the influence of dexmedetomidine.
Figure 3B:
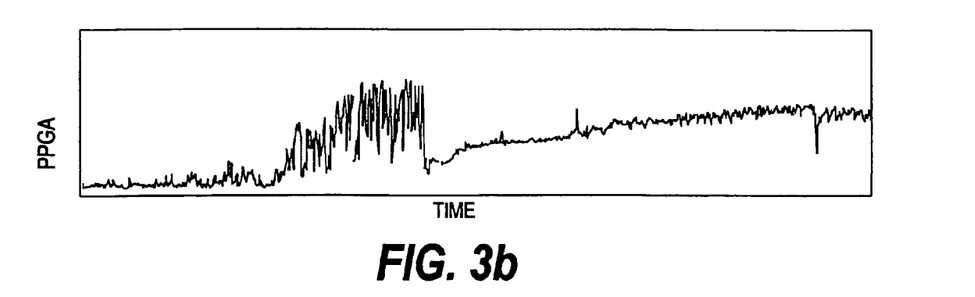
Figure 3C:
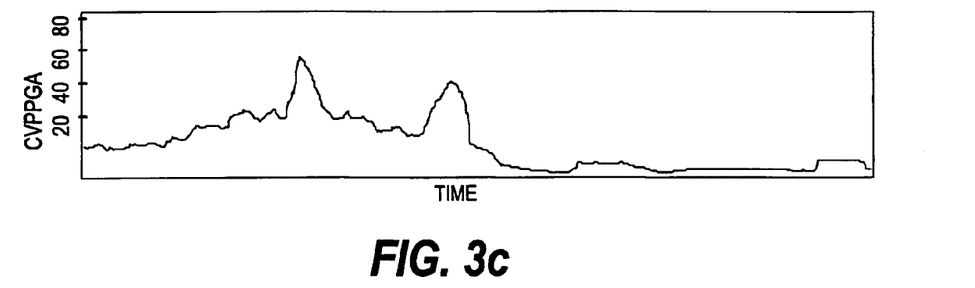

FIG. 3a to 3c are temporally aligned graphs illustrating a real measurement on a subject falling asleep under the influence of a sedative drug. FIG. 3a illustrates the entropy, FIG. 3b the photoplethysmographic amplitude, and FIG. 3c the coefficient of variation of the photoplethysmographic amplitude (CVPPGA) measured from the subject. As can be seen from FIG. 3c, the CVPPGA value remains low (in this example below ten) when the patient is in sleep. However, FIG. 3b indicates that photoplethysmographic amplitude cannot as such be used as the indicator of autonomic activity. This is due to the fact that the drugs used in ICU care and/or anesthesia may be vasoconstrictive or vasodilative, i.e. they may decrease or increase blood volume, thereby rendering the plethysmographic amplitude an invalid indicator of autonomic activity.

In the embodiment of FIG. 2, the indicator of autonomic activity is thus the CVPGA and the activity criterion is fulfilled if the CVPGA exceeds a predetermined limit value. However, any variable indicative of PGA variability may be used instead of CVPGA, such as the variance-to-mean ratio of the plethysmographic pulse amplitude. Another alternative is to calculate the ratio of the low frequency (LF) variability of the plethysmographic pulse amplitude to the high frequency (HF) variability of the plethysmographic pulse amplitude, i.e. so called sympatho-vagal ratio.

Instead of a plethysmographic signal, an ECG signal may also serve as the cardiovascular signal measured from the subject. The indicator of autonomic activity calculated based on the ECG signal data may be the heart rate variability (HRV) or the ratio of the low frequency HR variability to the high frequency HR variability.

The cardiovascular signal may also be a blood pressure (BP) signal, and the indicator of autonomic activity may be calculated as the ratio of the low frequency BP variability to the high frequency BP variability.

Moreover, any known index used to describe the sympatho-vagal balance may be utilized as the indicator of autonomic activity derived from the cardiovascular signal data.

The detection of the sleep/awake states may also be based on any parameter indicative of the level of hypnosis of the subject. Generally speaking, step 22 of FIG. 2 may thus include the determination of any parameter indicative of the hypnotic state of the subject (e.g. spectral edge frequency, delta band power etc.) One commonly used EEG-based commercial tool for assessing the level of sedation or hypnosis is the Bispectral Index, BIS™ (trademark of Aspect Medical Systems, Inc., 141 Needham Street, Newton, Mass. 02464, U.S.A.).

The BIS algorithm involves the calculation of three sub-indices, a spectral sub-index termed Beta Ratio, a bispectral sub-index termed SynchFastSlow, and a time-domain sub-index termed Burst Suppression Ratio. The resulting index is a combination of the three sub-indices. Therefore, step 14 in FIG. 1, or step 22 and 24 in FIG. 2, may also be based on a BIS™ value derived from the EEG signal data, or on one or more of the BIS™ sub-indices suitable for this purpose. For example, Beta Ratio and SynchFastSlow normally decrease as the patient approaches unconsciousness and might therefore be used as indicators of the sleep/awake states.

Figure 4:
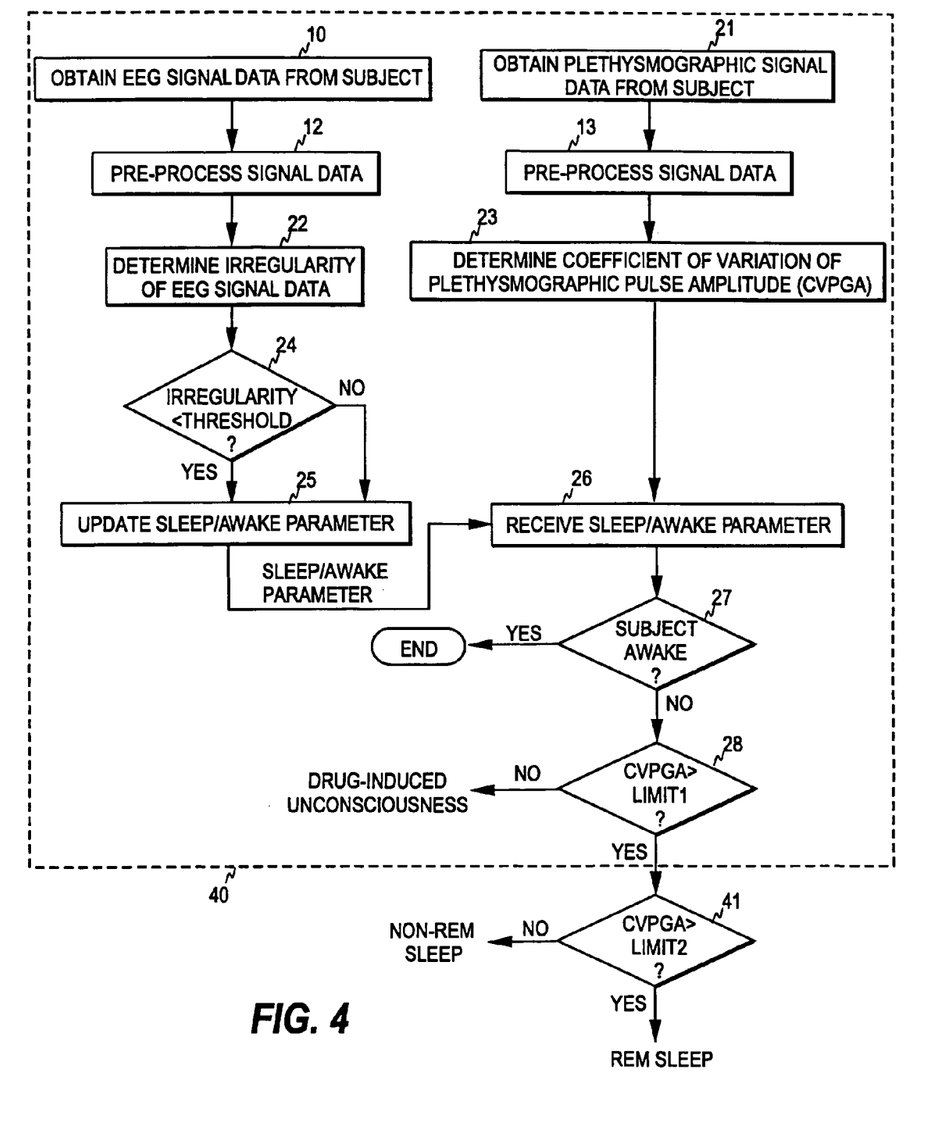
FIG. 4 is a flow diagram illustrating a further embodiment of the method of the invention.

In a further embodiment of the invention, the specificity of the method may be further improved by detecting whether a sleeping patient, i.e. a patient whose unconsciousness is not induced by drugs, is in a REM or non-REM sleep state. In this embodiment, which is illustrated in FIG. 4, an additional test is performed at step 41 to check whether the CVPGA also exceeds a second predetermined limit value higher than the first predetermined limit value. If this is the case, the process concludes that the subject is in REM sleep. If the CVPGA is between the first and second limit values, the process concludes that the subject is in non-REM sleep. This deduction is based on the findings according to which sympathetic-nerve activity and values of blood pressure and heart rate decline significantly during non-REM sleep but may increase during REM sleep even above levels recorded during wakefulness, cf. Somers et. al: *Sympathetic-Nerve Activity during Sleep in Normal Subjects*, The New England Journal of Medicine, vol. 328:303-307, Feb. 4, 1993.

Although it is assumed in FIG. 4 that the steps preceding step 41, which are denoted with a dashed box 40, correspond to the embodiment of FIG. 2, any of the embodiments discussed above may also be used for the enhanced embodiment of FIG. 4.

Figure 5A:
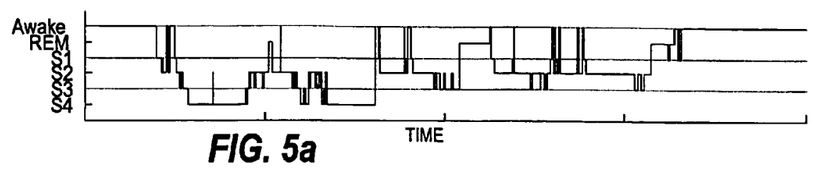
FIG. 5a illustrates different sleep stages of a subject sleeping naturally.
Figure 5B:
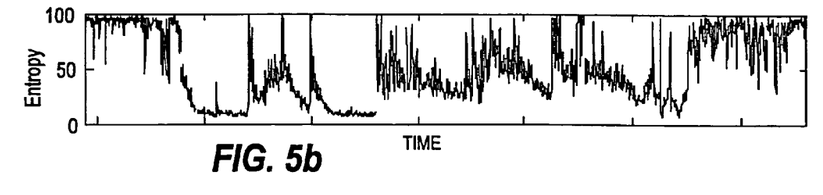
Figure 5C:
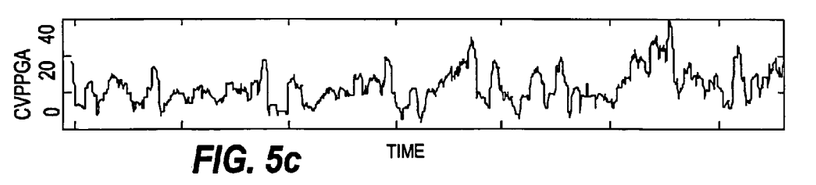

FIG. 5a to 5c are temporally aligned graphs illustrating the entropy and the coefficient of variation of the plethysmographic amplitude measured during different sleep stages of a subject sleeping naturally. FIG. 5a illustrates the sleep stages, while FIGS. 5b and 5c illustrate, respectively, the entropy and the PGA variability corresponding to the different stages of the sleep. As can be seen from FIGS. 5a and 5c, during sleep the highest CVPGA values are obtained during REM sleep.

Figure 6:
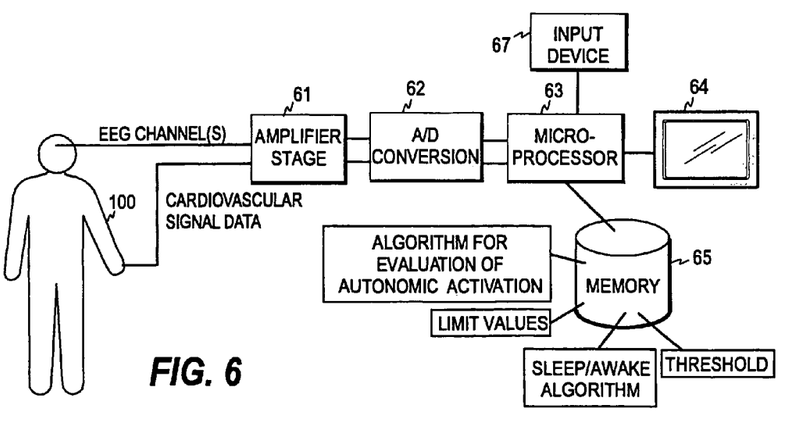
FIG. 6 illustrates one embodiment of the system or apparatus of the present invention.

FIG. 6 illustrates one embodiment of the system or apparatus according to the invention. In a hospital environment, the EEG signal is typically measured through an electrode arrangement attached to the facial area, especially to the frontal area of a subject 100. However, several EEG channels may also be measured and the EEG electrodes may be located around the entire scalp. If the cardiovascular signal is a PPG signal, it is typically measured from the tip of a finger.

The EEG signal(s) and the cardiovascular signal(s) obtained through the corresponding electrode arrangements are supplied to an amplifier stage 61, which amplifies the signal(s) before they are sampled and converted into digitized format in an A/D converter 62. The digitized signals are supplied to a computer unit 63 which may comprise one or more processors. For example, the system may be provided with dedicated data processing units for both signal types.

As discussed above, the signal path between each electrode arrangement and the computer unit may also be provided with various pre-processing stages, such as filtering stages, which serve to remove non-idealities from the measured signals. Moreover, the signal processing operations on the two signal paths may be implemented by common or dedicated processing units. Therefore, FIG. 6 only illustrates the basic operations applied to the signals, without taking a position on the actual hardware implementation.

The computer unit is provided with a memory or database 65, which may hold the digitized signal data obtained from the electrodes and the algorithms for the two measurements, i.e. a first algorithm for producing a sequence of a parameter indicative of sleep/awake states and a second algorithm for evaluating autonomic activity and for separating natural sleep from drug-induced sleep.

Using the stored algorithms and the associated parameters, i.e. the threshold for the parameter indicative of sleep/awake states and the limit values for the autonomic activation, the computer unit executes the functions described above and defines the state of the subject. The term computer unit here refers to any system, processor, circuit, or computing entity which is capable of computing the above variables based on EEG and cardiovascular signal data.

The user may supply information, such as the threshold and limit values required by the algorithms, through a user input device 67. The computer unit may display the result (drug-induced sleep/natural sleep/REM sleep/non-REM sleep) through at least one monitor 64 connected to the computer unit. The values of any of the above parameters may also be displayed, either as a continuously updated numeric value or as a graph.

Although one computer unit or processor may perform the above steps, the processing of the data may also be distributed among different units/processors (servers) within a network, such as a hospital LAN (local area network). The apparatus of the invention may thus also be implemented as a distributed system. However, the implementation of the apparatus as a compact monitoring unit, which may be movable with the patient, allows the monitoring of the patient to be continued in a post anesthetic care unit, for example.

The above embodiments concern automated monitoring methods in which the sleep state of a subject is detected based on EEG signal data. However, as mentioned above, the detection of the sleep/awake states may also be based on any known parameter indicative of the level of hypnosis of the subject. For the determination of the parameter, different types of signals indicative of brain activity may be utilized. For example, instead of EEG signal data magnetoencelographic (MEG) signal data may be employed. MEG is indicative of the magnetic component of brain activity, i.e. it is the magnetic counterpart of EEG. The detection of sleep may also be based on various sensors that record the movements of the subject.

Furthermore, it is not necessary to use an automated sleep detection mechanism, but the sleep state may also be detected by the nursing staff. This detection may be based on a visual observation of the subject, and for the detection and the associated decision-making the system of the invention may or may not provide a supporting parameter indicative of the level of hypnosis of the subject. Thus, in a simplified embodiment the invention does not include the measurement of a brain wave signal and the associated algorithm for producing a sequence of a parameter indicative of sleep/awake states.

An existing patient monitor, or a monitoring system, providing cardiovascular data may also be upgraded to enable the separation of natural sleep from drug-induced unconsciousness. Such an upgrade may be implemented by delivering to the patient monitor a software module that enables the system to process the cardiovascular data in the above-described manner. The software module may be delivered, for example, on a data carrier, such as a CD or a memory card, or through a telecommunications network. As obvious from the above, in a non-automated system the software module may process only cardiovascular data, whereas in an automated system the software module further comprises a code portion configured to detect, based on brain signal data, when the subject is in sleep, and to notify the code portion performing the identification of the type of sleep.

The software module may receive the cardiovascular data and the possible brain wave signal data in real-time directly from the corresponding electrode arrays or from the memory of the monitoring system upon storage of the data. In the latter case, the signals may already be temporally aligned by time stamps attached to the signal values. In this case the software module may also be in a device which may not be able to perform the actual measurements, but only the calculation of the results after the signal data has been measured by another device/system. For example, a monitoring device located in a supervision room may retrieve signal data measured by a bedside monitor. Generally, the operations performed in the software module depend on the operations performed in the existing monitor/system. For example, the existing monitor/system may determine EEG entropy, whereby the upgrade module may utilize the entropy value sequence determined.

Although the invention was described above with reference to the examples shown in the appended drawings, it is obvious that the invention is not limited to these, but may be modified by those skilled in the art without departing from the scope and spirit of the invention.

The invention claimed is:

1. A method for separating natural sleep from drug-induced unconsciousness, the method comprising the steps of:
acquiring brain wave signal data from a subject;
detecting, based on the brain wave signal data, when the subject is in sleep;
obtaining cardiovascular signal data from the subject, the cardiovascular signal data being indicative of the function of the cardiovascular system of the subject;
deriving, using a processor based on the cardiovascular signal data, an indicator indicative of the activation of the autonomic nervous system of the subject; and
wherein when the detecting step indicates that the subject is in sleep, identifying, based on the indicator, whether the sleep is drug-induced sleep or natural sleep.

2. A method according to claim 1, wherein the obtaining step includes obtaining the cardiovascular signal data from the subject, in which the cardiovascular signal data corresponds to one of the data types in a group including plethysmographic data, EGG data, and blood pressure data.

3. A method according to claim 1, wherein the detecting step includes a sub-step of determining a parameter indicative of the hypnotic state of the subject.

4. A method according to claim 3, wherein the determining sub-step includes determining the parameter, in which the parameter is a measure of irregularity of the brain wave signal data.

5. A method according to claim 4, wherein the determining sub-step includes determining the measure of irregularity of the brain wave signal data, in which the measure of irregularity is indicative of the entropy of the brain wave signal data.

6. A method according to claim 5, wherein the detecting step includes the sub-steps of:
comparing the measure of irregularity with a threshold value; and
deciding that the subject is in sleep if the measure of irregularity is below the threshold value.

7. A method according to claim 1, wherein the detecting step includes the sub-steps of:
defining at least two sub-indices from the brain wave signal data, the at least two sub-indices being selected from a group including a spectral sub-index, a bispectral sub-index, and a time-domain sub-index; and
deriving a combinatory index from the at least two sub-indices.

8. A method according to claim 1, wherein the identifying step includes a sub-step of comparing the indicator with a first limit value.

9. A method according to claim 1, wherein
the obtaining step includes obtaining the cardiovascular signal data from the subject, in which the cardiovascular signal data is plethysmographic data; and
the deriving step includes deriving the indicator, in which the indicator is indicative of the variability of plethysmographic pulse amplitude.

10. A method according to claim 8, wherein the identifying step includes the sub-steps of:
indicating natural sleep when the indicator exceeds the first limit value; and
indicating drug-induced unconsciousness when the indicator remains below the first limit value.

11. A method according to claim 10, further comprising a step of comparing the indicator with a second limit value greater than the first limit value, the comparing step being performed when the indicator exceeds the first limit value.

12. A method according to claim 11, further comprising the steps of:
indicating REM sleep when the indicator exceeds the second limit value; and
indicating non-REM sleep when the indicator is between the first limit value and the second limit value.

13. An arrangement for separating natural sleep from drug-induced unconsciousness, the arrangement comprising:
first measurement means for obtaining cardiovascular signal data from a subject, the cardiovascular signal data being indicative of the function of the cardiovascular system of the subject;
calculation means for deriving, based on the cardiovascular signal data, an indicator indicative of the activation of the autonomic nervous system of the subject;
second measurement means for acquiring brain wave signal data from the subject;
sleep detection means for detecting, based on the brain wave signal data, when the subject is in sleep; and
identification means for identifying, based on the indicator and notification from the sleep detection means that the subject is in sleep, whether the sleep is drug-induced sleep or natural sleep.

14. An arrangement according to claim 13, wherein the first measurement means are constructed to obtain signal data whose type corresponds to one of the data types in a group including plethysmographic data, ECG data, and blood pressure data.

15. An arrangement according to claim 13, wherein the sleep detection means are configured to determine a measure of irregularity of the brain wave signal data.

16. An arrangement according to claim 15, wherein the measure of irregularity is indicative of the entropy of the brain wave signal data.

17. An arrangement according to claim 13, wherein the sleep detection means are configured to determine
at least two sub-indices from the brain wave signal data, the at least two sub-indices being selected from a group including a spectral sub-index, a bispectral sub-index, and a time-domain sub-index and
a combinatory index from the at least two sub-indices.

18. An arrangement according to claim 13, wherein the identification means are configured to compare the indicator with a first limit value.

19. An arrangement according to claim 18, wherein the identification means are further constructed to indicate natural sleep when the indicator exceeds the first limit value and drug-induced unconsciousness when the indicator remains below the first limit value.

20. An arrangement according to claim 19, wherein the identification means are further constructed to compare the indicator with a second limit value greater than the first limit value.

21. An arrangement according to claim 20, wherein the identification means are further constructed to indicate REM sleep when the indicator exceeds the second limit value and non-REM sleep when the indicator is between the first limit value and the second limit value.

22. An arrangement according to claim 13, wherein
the first measurement means are constructed to obtain plethysmographic signal data from the subject; and
the calculation means are constructed to derive the indicator, in which the indicator is indicative of the variability of plethysmographic pulse amplitude.

23. An arrangement according to claim 15, wherein the sleep detection means are constructed to compare the measure of irregularity with a threshold value and decide that the subject is in sleep if the measure of irregularity is below the threshold value.

24. An arrangement for separating natural sleep from drug-induced unconsciousness, the arrangement comprising:
- a first measurement module that obtains cardiovascular signal data from a subject, the cardiovascular signal data being indicative of the function of the cardiovascular system of the subject;
- a second measurement module that acquires brain wave signal data from the subject;
- a first data processor module that detects, based on the brain wave signal data, when the subject is in sleep,
- a second data processor module that derives, based on the cardiovascular signal data, an indicator indicative of the activation of the autonomic nervous system of the subject; and
- a third data processor module that identifies, based on the indicator, whether the sleep is drug-induced sleep or natural sleep,
- wherein the first data processor module is configured to notify the second data processor module of the sleep.

25. A computer program product for separating natural sleep from drug-induced unconsciousness, the computer program product comprising:
- a first program code portion configured to derive, based on cardiovascular signal data measured from a subject, an indicator indicative of the activation of the autonomic nervous system of the subject; and
- a second program code portion configured to detect, based on brain signal data measured from the subject, when the subject is in sleep,
- a third program code portion configured to identify, based on notification from the second program code when the subject is in sleep and the indicator, whether the sleep is drug-induced sleep or natural sleep.

* * * * *

UNITED STATES PATENT AND TRADEMARK OFFICE
CERTIFICATE OF CORRECTION

| | |
|---|---|
| PATENT NO. | : 7,630,758 B2 |
| APPLICATION NO. | : 11/473223 |
| DATED | : December 8, 2009 |
| INVENTOR(S) | : Lapinlampi et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 674 days.

Signed and Sealed this

Second Day of November, 2010

David J. Kappos
*Director of the United States Patent and Trademark Office*